United States Patent [19]

Niswender et al.

[11] 4,082,738

[45] Apr. 4, 1978

[54] CYANOCOBALAMIN DERIVATIVES

[75] Inventors: Gordon Dean Niswender; James M. Hudson, both of Fort Collins, Colo.

[73] Assignee: Rohm and Haas Company, Philadelphia, Pa.

[21] Appl. No.: 689,280

[22] Filed: May 24, 1976

Related U.S. Application Data

[62] Division of Ser. No. 552,919, Feb. 25, 1975, Pat. No. 3,981,863.

[51] Int. Cl.² .............................. A23J 1/08; A23J 1/06
[52] U.S. Cl. ................................ 260/121; 260/112 R; 260/112 B
[58] Field of Search ........................... 260/112 R, 121

[56] References Cited

U.S. PATENT DOCUMENTS 3,035,983  5/1962  Sherlock ..................... 260/112 R X
3,042,588  7/1962  Heathcote ................... 260/112 R X

OTHER PUBLICATIONS

Gregory et al., Nature, 173, p. 830 (1954).

Wijmenga et al., Chemical Abstracts, vol. 48:5315h (1954).
DiCarlo et al., Chemical Abstracts, vol. 67:2061c (1967).
Haffner et al., Chemical Abstracts, vol. 79:103,343z (1973).

*Primary Examiner*—Walter C. Danison

[57] ABSTRACT

The present invention is concerned with novel derivatives of cyanocobalamin (vitamin $B_{12}$), especially of the monocarboxylic acid hydrolysates thereof, by which (1) an antigenic conjugate thereof with a protein is obtainable and (2) a readily iodinatable aromatic ring can be introduced while retaining in each instance, the essential constitution of cyanocobalamin to such an extent that (a) the antigenic protein conjugate, when introduced into the blood stream of a vertebrate, causes the formation of an antibody which is specific to the cyanocobalamin portion of the conjugate and (b) unmodified cyanocobalamin and the second-mentioned derivative when tagged or labeled with radioactive-iodine competitively bind on the aforementioned antibody. Thus, the present invention provides cyanocobalamin derivatives which are quite useful in radioimmunoassay (RIA) of vitamin $B_{12}$.

2 Claims, No Drawings

CYANOCOBALAMIN DERIVATIVES

This is a division of application Ser. No. 552,919 filed Feb. 25, 1975 now U.S. Pat. No. 3,981,863.

DESCRIPTION OF THE INVENTION

It is known that vitamin $B_{12}$ can be converted to a monocarboxylic acid or mixture thereof by hydrolysis under mild acid conditions without accompanying hydrolysis of the ribofuranosidophosphorylpropionamide side chain (J.C.S. (1953), 3848–3864). It is thought that the main monocarboxylic hydrolysis product of the invention is that in which the $-CH_2CONH_2$ group of the pyrrole nucleus carrying the "ribo—" side chain is converted to $-CH_2COOH$. However, the product may also contain an appreciable amount of one or more other monocarboxylic hydrolysates in which a different terminal amide ($-CONH_2$) group (e.g., the $-CH_2CH_2CONH_2$ or the $-CH_2CONH_2$ on one of the other three pyrrole nuclei) is converted to a carboxyl group.

In accordance with the present invention, the monocarboxylic product thus obtained is reacted with a p-(aminoalkyl)phenol to introduce a phenolic group into the vitamin $B_{12}$ derivative. The reactant that may be so used may be any compound of the general formula:

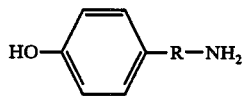

(I)

in which R is an alkylene group having 1 to 18, preferably 1 to 3, carbon atoms which may be substituted with an element or group other than an amino or unesterified carboxylic acid group.

Examples of the compounds that may be so used are:
p-(aminomethyl)phenol
p-(β-aminoethyl)phenol(tyramine)
p-(3-aminopropyl)phenol
p-(2-aminopropyl)phenol One of the preferred groups of compounds that may be so used are the alkyl esters of tyrosine having the formula:

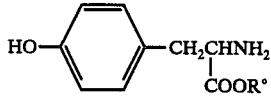

(II)

wherein R° is an alkyl group having from 1 to 18, preferably from 1 to 2 carbon atoms, such as the methyl or ethyl ester of tyrosine.

The preferred reactant compounds are tyramine and that of Formula II wherein R° is methyl. These compounds serve to produce a phenolic group having both ortho positions (with respect to the hydroxyl group) available and receptive to halogenation.

In general the reaction of the vitamin $B_{12}$ monocarboxylic acid with the aminoalkyl-containing phenol of Formula I or II is carried out in a solvent medium containing a tertiary amine at a low temperature in the range of about 0° to 20° C. A small amount of a chloroformic acid ester of a lower alkanol having 1 to 4 carbon atoms is used as a self-regenerating intermediate that serves as a reaction-facilitating vehicle or interchanging agent by forming an anhydride with the vitamin $B_{12}$ monocarboxylic acid that hydrolyzes in the presence of the amine of Formula I or II, which, in turn, results in the formation of an amide of the vitamin $B_{12}$ monocarboxylic acid, the amide linkage serving to couple or conjugate a phenolic ring to the vitamin $B_{12}$. A preferred chloroformate is the isobutyl ester which forms an anhydride that is particularly prone to hydrolyze under the conditions of the reaction. The amine of Formula I or II is added after the chloroformate has reacted. Then an inorganic alkaline material, e.g., caustic soda or potash, is added.

The reaction may be illustrated by the following sequence of steps, using R'COOH to represent the vitamin $B_{12}$ monocarboxylic acid,

as the chloroformate ester, and R'''$NH_2$ as the amine of Formula I or II:

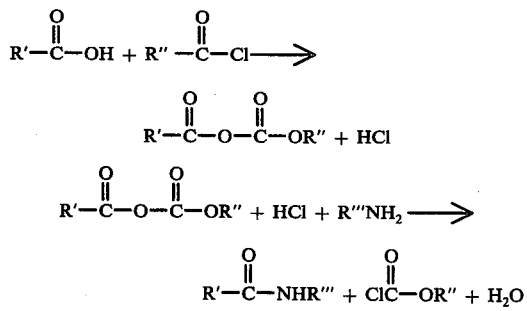

Thus, the product has a hydroxyphenyl group linked to the vitamin $B_{12}$ through an amidoalkyl linkage connected to the phenyl group in the position para to the phenolic hydroxyl. It may be, and hereinafter it is sometimes, called a vitamin $B_{12}$ phenol conjugate.

The resulting vitamin $B_{12}$ derivative (phenol conjugate) is readily iodinated to introduce one of the radioactive iodine isotopes ($^{125}I$ and $^{131}I$) into one or both of the two positions of the phenolic group ortho to the hydroxyl group. Such iodination, for example, can be effected by mixing the $B_{12}$ phenol conjugate in an aqueous solution of sodium iodide in which the anion is one of the radioactive isotopes of iodine, such as mentioned above, and an oxidizing agent, such as Chloramine T. Optionally, but preferably, the aqueous reaction medium is buffered at a pH of 6 to 8, preferably about 7.4. After completion of the reaction, a reducing agent is added to neutralize any residual oxidizing agent and the iodinated vitamin $B_{12}$ phenol conjugate is then separated from free radioactive iodine, as by electrophoresis or column chromatography.

Besides making the vitamin $B_{12}$ phenol conjugate and its radioiodinated product from the vitamin $B_{12}$ monocarboxylic acid, a portion of the latter is covalently bonded with a protein of sufficiently high molecular weight, such as from 10,000 to 300,000 or even up to a million or more, to convert the vitamin $B_{12}$ (normally a hapten) into an antigen that can be injected into the blood stream of a vertebrate, such as a rabbit, hamster, or sheep, to develop an antibody that is specific for vitamin $B_{12}$ and can be used in RIA procedures to assay body fluids for their content of vitamin $B_{12}$.

Examples of protein that can be covalently bonded with the vitamin $B_{12}$ by reaction with the carboxylic group include blood proteins generally having molecular weights in the range of 3 million to 20 million; and the globulins, albumins, and fibrinogens having molecular weights in the range of 100,000 to a million. Specifically, bovine serum albumin, sheep serum albumin, rabbit serum albumin, goat serum albumin, polysine, thyroglobulin, and gamma-globulin may be used.

The same general procedure described above for making the vitamin $B_{12}$ phenol conjugate can be used for making the vitamin $B_{12}$-protein conjugate from the $B_{12}$ monocarboxylic acid using the protein in place of the amine of Formula I or II.

The following procedures are illustrative of the present invention. In these procedures, the letter u of the English alphabet is used in place of the customary Greek letter $\mu$ to represent the prefix "micro" when placed before an abbreviation of a unit of measure.

EXAMPLE A

Preparation of Monocarboxylic Acids of Vitamin $B_{12}$. J.C.S. (1953) 3849

Vitamin $B_{12}$ (1 gram) is dissolved in 0.1N hydrochloric acid (200 cc) and the solution is kept in the dark at room temperature for 60 hours.

The following procedures are carried out in a darkened laboratory: the solution is then adjusted to pH 4 with base (dilute NaOH) and placed on a column of acid-washed alumina (4 × 60 cm). The greater part of the unchanged $B_{12}$ is eluted with approximately 500 ml of water. The column is then washed with 0.1N ammonium hydroxide until the red acidic pigments are removed. This eluent is concentrated in vacuo on a rotary evaporator at 40° C. to a small volume and then made acid to pH 4 with concentrated HCl. The acids are then precipitated by the addition of acetone, allowed to stand overnight at 0° C., then filtered off and washed with acetone on the filter. The solid is dried at 100° C. in vacuo for 10 minutes to yield 180 mg of deep-red crystals, 18%.

EXAMPLE 1

Vitamin $B_{12}$-BSA Conjugate

Fifty mg of $B_{12}$ monocarboxylic acid obtained from Example A is dissolved in 1.5 ml of dry dimethylformamide (DMF) and treated with 25 ul of tri-n-butylamine. The solution is cooled to 0° C. Then 15 ul of isobutyl chloroformate is added and stirring is continued for 20 minutes at 0° C. This is then added in one portion to a cold solution of 50 mg of bovine serum albumin (BSA) in 5 ml of 50% aqueous DMF and 50 ul of 1N NaOH. Stirring is continued in an ice-bath for one hour and an additional 25 ul of 1N NaOH is added. The mixture is then stirred 3 more hours in an ice-bath and then the mixture is dialyzed for 72 hrs. against running water. The dialysate is adjusted to pH 4.5 with dilute HCl. The precipitated vitamin $B_{12}$-BSA conjugate is separated by centrifugation, redissolved in water and lyophilized by freeze-drying. Yield: 65 mg.

EXAMPLE 2

By the procedure of Example 1, $B_{12}$-protein conjugates are obtained from the following proteins:
(a) Sheep serum albumin (SSA)
(b) Rabbit gamma-globulin (RGG)
(c) Porcine serum albumin (PSA)

EXAMPLE 3

Vitamin $B_{12}$-Tyrosine Methyl Ester Conjugate ($B_{12}$-TME Conjugate)

Forty mg of $B_{12}$ monocarboxylic acids obtained in Example A is dissolved in 1.5 ml of dry dimethylformamide and treated with 8 ul of tri-n-butylamine. The solution is cooled to 0° C., 5 ul of isobutyl chloroformate is then added and the mixture stirred for 20 minutes at 0° C. A cold solution of tyrosine methyl ester hydrochloride (8 mg) in 3 ml of 50% aqueous DMF and 50 ul 1N NaOH is then added and the solution is stirred at 0° C. and allowed slowly to come to room temperature overnight. The solution is then poured into 20 ml of cold water and concentrated in vacuo at 40° C. to approximately one-fourth its volume and acetone is added to precipitate the compound. The filtered products are dissolved in methanol and the insoluble residues filtered off. The methanol solution is treated with acetone and the resulting precipitated compound collected by filtration, washed with acetone and dried to yield 43 gm of vitamin $B_{12}$ conjugate of the methyl ester of tyrosine as red crystals.

EXAMPLE 4

By the same procedure as in Example 3, the vitamin $B_{12}$ conjugate of tyramine is obtained.

EXAMPLE 5

The procedure of Example 3 is followed except the methyl ester of tyrosine is replaced with an equivalent amount of the corresponding ethyl ester, thereby producing the vitamin $B_{12}$ conjugate of the ethyl ester of tyrosine.

EXAMPLE 6

The vitamin $B_{12}$ conjugate of the n-butyl ester of tyrosine is obtained by the procedure of Example 3, substituting an equivalent amount of tyrosine n-butyl ester for the tyrosine methyl ester.

EXAMPLE 7

The product ($B_{12}$-TME conjugate) of Example 3 is labeled with $^{125}I$ as follows:

To 2.5 ug of the product, there is added (1) 50 ul of 0.5M phosphate buffer containing 1 mCi of Na $^{125}I$ and (2) 30 ug Chloramine T. (The buffer solution to which the Na $^{125}I$ is added consists of 34 g of $KH_2PO_4$ and 35.5 g of anhydrous $Na_2HPO_4$ per liter of water.) The reaction mixture is agitated for 30 seconds and then 60 ug of sodium metabisulfite is added. The iodinated conjugate is then separated from free $^{125}I$ by column chromatography.

EXAMPLE 8

The procedure of Example 7 is repeated replacing the $B_{12}$-TME conjugate with a respective one of the corresponding tyramine, tyrosine ethyl ester, and tyrosine n-butyl ester conjugates of vitamin $B_{12}$ obtained in Examples 4, 5 and 6 respectively, producing corresponding radioactive $^{125}I$ labeled products.

EXAMPLE 9

The procedure of Example 7 is repeated except the Na $^{125}I$ is replaced by Na $^{131}I$.

EXAMPLE 10

The procedure of Example 7 is repeated replacing the $B_{12}$-TME conjugate with a respective one of the corresponding p-(18 aminooctadecyl)-phenol, tyrosine lauryl ester, and tyrosine stearyl ester conjugates of vitamin $B_{12}$ obtained in Examples 4, 5 and 6 respectively, producing corresponding radioactive $^{125}I$ labeled products.

EXAMPLE 11

For RIA determination of Vitamin $B_{12}$, the following solutions and blood sera are used:

A. 0.01M Phosphate buffer solution (PBS) which contains 0.68g $KH_2PO_4$ and 0.71g anhydrous $Na_2HPO_4$ in one liter of water, herein referred to as Buffer A.

B. The same solution as in A except it also contains 1.46g (0.05M) per liter of ethylenediaminetetracetic acid, herein referred to as Buffer B.

C. The first antibody serum against Vitamin $B_{12}$ obtained from the blood serum of a rabbit that has been injected with the product from Example 1.

D. Normal rabbit serum obtained from a rabbit which has not been so inoculated.

E. A second antibody serum obtained from the blood serum of a sheep injected with the gamma globulins of a normal rabbit.

F. A first antibody solution prepared by diluting 0.3125ml of the antibody serum from C above and 5.9375ml of normal rabbit serum in D above to 1 liter with water. 40ml of the resulting solution is diluted to 1 liter with Buffer B.

G. A second antibody solution prepared by diluting 0.714ml of the second antibody serum from E to 25 ml with Buffer B.

H. Human blood serum taken from a person whose Vitamin $B_{12}$ level is to be determined.

The assay is performed using the following procedure:

1. Add 100ul of serum H to a 12 × 75mm glass test tube.
2. Add thereto 550ul of Buffer A containing 1.1mg of subtilisin enzyme. Mix gently.
3. Incubate at 37° C, for one hour.
4. Place in boiling water bath for 10 minutes; then cool to room temperature.
5. Add 100ul of $^{125}I$-Vitamin $B_{12}$-TME as prepared in Example 7.
6. Add 100ul of first antibody solution (F above). Vortex.
7. Incubate 4 hours at room temperature.
8. Add 100 ul of second antibody solution (G above). Vortex.
9. Incubate 12 hours at room temperature.
10. Add 3ml cold (4° C.) Buffer A solution.
11. Centrifuge cold (4° C.) at 1000 × g for 30 minutes.
12. Decant supernatant and discard.
13. Count precipitate using a gamma counter.

The concentration of Vitamin $B_{12}$ in the human serum is determined in the usual way from a standard curve prepared from solutions of Vitamin $B_{12}$ of known concentration treated as above.

The radioactive iodine isotope labeled vitamin $B_{12}$ derivatives show marked specific activity and sensitivity in assay, particularly when minute amounts of $B_{12}$ are to be assayed in human body fluids, such as blood serum or plasma. These iodine-labeled $B_{12}$ derivatives are reasonably stable and do not require liquid scintillation counting analysis of the samples.

We claim:

1. A vitamin $B_{12}$ protein conjugate in which a protein selected from bovine serum albumin, sheep serum albumin, rabbit serum albumin, goat serum albumin, polysine, thyroglobulin or gamma-globulin is covalently bonded through one of the $CH_2CH_2CONH_2$ or $-CH_2CONH_2$ groups initially present in one of the pyrrole nucleus of the vitamin $B_{12}$ molecule.

2. Vitamin $B_{12}$-bovine serum albumin conjugate in accordance with claim 1.

* * * * *

UNITED STATES PATENT AND TRADEMARK OFFICE
CERTIFICATE OF CORRECTION

PATENT NO. : 4,082,738

DATED : April 4, 1978

INVENTOR(S) : Gordon Dean Niswender and James H. Hudson

It is certified that error appears in the above-identified patent and that said Letters Patent are hereby corrected as shown below:

Col. 4, l. 23, delete "gm" after number 43 and in lieu of insert -- mg --.

Signed and Sealed this

Ninth Day of January 1979

[SEAL]

Attest:

RUTH C. MASON
Attesting Officer

DONALD W. BANNER
Commissioner of Patents and Trademarks